United States Patent [19]

Tucker et al.

[11] 4,258,711

[45] Mar. 31, 1981

[54] INFUSION APPARATUS AND METHOD

[75] Inventors: Elton M. Tucker, Medfield; Frank R. Prosl, Duxbury, both of Mass.

[73] Assignee: Metal Bellows Corporation, Sharon, Mass.

[21] Appl. No.: 76,169

[22] Filed: Sep. 17, 1979

Related U.S. Application Data

[60] Division of Ser. No. 9,756, Feb. 5, 1979, Pat. No. 4,193,397, which is a continuation-in-part of Ser. No. 856,558, Dec. 1, 1977, abandoned.

[51] Int. Cl.³ ............................................. A61M 31/00
[52] U.S. Cl. ........................... 128/207.19; 128/214 F; 128/DIG. 12
[58] Field of Search ............... 128/207.19, 214 F, 172, 128/260, 213 R, 268, DIG. 12

[56] References Cited

U.S. PATENT DOCUMENTS

| | | | |
|---|---|---|---|
| 3,840,009 | 10/1974 | Michaels et al. | 128/172 |
| 3,923,060 | 12/1975 | Ellinwood, Jr. | 128/214 F |
| 4,013,074 | 3/1977 | Siposs | 128/214 F |
| 4,056,095 | 11/1977 | Rey et al. | 128/260 |
| 4,077,405 | 3/1978 | Haerten et al. | 128/214 F |
| 4,137,913 | 2/1979 | Georgi | 128/214 F |
| 4,146,029 | 3/1979 | Ellinwood, Jr. | 128/260 |
| 4,193,397 | 3/1980 | Tucker et al. | 128/207.19 |

*Primary Examiner*—John D. Yasko
*Attorney, Agent, or Firm*—Cesari and McKenna

[57] ABSTRACT

An infusion apparatus and method employs an infusate reservoir connected by way of a first flow path having a first flow restrictor to a mixing chamber. The reservoir is also connected by a second flow path having a second flow restrictor to the same mixing chamber so that infusate may be conveyed to the chamber at different rates. A normally closed valve is provided in the second flow path so that infusate flows from the two paths supplement one another in the mixing chamber only when the valve is open. The reservoir and chamber volumes, infusate concentration and chamber outlet flow rate are selected to provide an integrated dosage profile suited to the patient.

12 Claims, 14 Drawing Figures

INFUSION APPARATUS AND METHOD

RELATED APPLICATION

This application is a division of applicaton Ser. No. 9,756 filed Feb. 5, 1979, entitled Implantable Infusion System now U.S. Pat. No. 4,193,397; which in turn was a continuation in part of application Ser. No. 956,558 filed Dec. 1, 1977 entitled Implantable Infusion System, now abandoned.

BACKGROUND OF THE INVENTION

This invention relates to an infusion apparatus and method. It relates more especially to an improved infusion method rechargeable implantable pump for conducting infusate to a selected site in a living body.

Relatively recently, an infusion apparatus has been developed which can be implanted in the body to remain there for a prolonged period. The apparatus can be refilled with infusate without having to remove the apparatus. Refilling is achieved simply by injecting additional infusate through a penetrable septum in the apparatus, which septum is located directly under the patient's skin. In some cases, the act of refilling the apparatus with infusate also recharges the apparatus' power source so that the device can operate uninterruptedly to dispense infusate such as insulin or heparin at a very small flow rate for a prolonged period. An example of infusion apparatus of this general type is disclosed in U.S. Pat. No. 3,731,681.

It has also been proposed to control the infusate flow from such apparatus by means of a valve controlled by a programmable controller so that the dosage rate can be varied to suit particular needs of the patient. For example, in the case of insulin, ideally the patient should receive a small continuous or basal dose to satisfy a particular steady state requirement that depends upon the average amount of sugar in his blood. Then immediately after a meal when blood sugar level rises dramatically, the infusion apparatus should dispense a much larger dose (prolonged bolus) of insulin to offset the increased sugar level caused by the ingestion of the meal. One such programmable infusion apparatus, described in U.S. Pat. No. 4,077,405, varies the valve control pulses in frequency and/or duration to control the duty cycle of an electrically operated valve to provide the requisite basal and bolus doses at the requisite times.

Problems with prior infusion apparatus of the type described above arises because the basal and bolus doses have the same concentration since they both originate from the same infusate reservoir inside the apparatus and incorporation of the necessary batteries, valves and electronic system may reduce system reliability. With the bolus insulin rate requirement being ten to fifteen times that of the basal rate, it will become obvious that the mean insulin requirement will quickly consume the reservoir volume if the concentration is set to meet the requirement of the basal condition. The desirability of the system is further reduced due to the need for the batteries for the electrical power source. These must be periodically recharged or replaced. Furthermore, the infusate reservoir has to be quite large to provide both basal and bolus flows while at the same time avoiding the need for frequent refilling. The large reservoir of course increases the overall size and weight of the pump package implanted in the body to the discomfort of the patient.

Prior controllable infusion apparatus is disadvantaged also in that it is possible for the patient to inadvertently or intentionally control the apparatus so as to administer an overdose of infusate. This not only exhausts the supply of infusate but also can result in injury to the patient. An insulin overdose, for example, can bring on hypoglycemic shock resulting in death to the patient.

More generally, however, it would be desirable to provide implantable infusion apparatus which is small and compact so as to occupy a minimum amount of space in the body, yet which is able to supply the patient's infusate needs while still avoiding the need for frequent refills or consumable power sources such as batteries.

SUMMARY OF THE INVENTION

Accordingly it is an object of the present invention to provide improved implantable infusion apparatus which can dispense infusate to a selected site in the body at a very small flow rate continuously for a prolonged period.

Another object of the invention is to provide infusion apparatus of this type which can dispense infusate of various types to the patient in a plurality of different concentrations.

A further object of the invention is to provide infusion apparatus of this general type which provide both the basal and bolus infusate needs of a patient for a prolonged period, yet which is still relatively small and compact.

Another object of the invention is to provide such apparatus whose bolus infusion is patient-actuated, yet which avoids the possibility of a patient-administered infusate overdose.

Another object is to provide such apparatus which does not require use of a battery powered source.

A further object is to provide apparatus of the type which provides improved bolus infusate flow control.

It is a more general object of the present invention to provide implantable infusion apparatus which permits the use of dual infusion means providing infusate in different concentrations or different kinds under separate control.

Still another object is to provide an infusion method which permits great flexibility in the selection of the dosage to the patient.

Other objects will in part be obvious and will in part appear hereinafter.

The invention accordingly comprises the combination of steps, the features of construction, the combination of elements and the arrangement of parts as will be exemplified in the following detailed description, and the scope of the invention will be indicated in the claims.

Infusion apparatus of the type with which we are concerned here has particular application as a so-called artificial pancreas to dispense insulin to a diabetic patient to counteract excessive glucose present in the patient's bloodstream. Accordingly we will describe the invention in that context. It should be understood, however, that the apparatus can be used to dispense a variety of other infusates into a human or animal body for various purposes.

The average diabetic should receive a basal dosage of insulin continuously in response to changes in the level of glucose in his bloodstream. In addition, he should receive larger, short-term so-called bolus doses of insulin to offset much higher short-term glucose levels in the bloodstream which may be present particularly after meals. Moreover the bolus doses should be introduced into the bloodstream and take effect as soon as possible and should terminate as the glucose level is returned to its basal state. The present invention accomplishes these objectives without implanted electrical power and with a small compact package which occupies a minimum amount of space in the body.

Instead of dispensing insulin of a given concentration to the infusion site from a single reservoir at different rates to provide the basal and bolus doses to the patient, a plurality of reservoirs are employed each operating independently and complimenting the other. Thus, the apparatus includes a main (basal) reservoir to supply the patient's basal dosage requirement and a secondary (bolus) reservoir to provide the bolus doses. The main basal reservoir has an outlet including the filter and flow restricter. Likewise the bolus reservoir has an outlet including a separate filter and flow restricter. The outlets of the two reservoirss join at a small mixing chamber downstream from their flow restricters and suitable tubing leads from the mixing chamber to the infusion site in the patient's body. Located in the outlet from the bolus reservoir between its flow restricter and the mixing chamber is a normally closed valve. When the valve is closed, infusate flows only from the basal reservoir to the mixing chamber and thence to the infusion site. On the other hand when the valve is open, the infusate flow from the basal reservoir is supplemented by the flow from the bolus chamber.

Preferably each reservoir is of the type disclosed in U.S. Pat. No. 3,731,681 comprising a variable volume infusate chamber which is collapsed by the pressure exerted by a confined two-phase fluid which vaporizes at physiological temperatures so as to exert sufficient pressure on the chamber walls to expel the infusate from the chamber to the infusion site. However, other types of infusate reservoirs can be employed. One such other reservoir is disclosed in U.S. Pat. No. 3,894,538.

Preferably also, provision is made for refilling each infusate reservoir by injecting fresh infusate through a penetrable septum in an inlet passage leading to the infusate chamber and located directly under the patient's skin. The refilling operation also recharges the reservoir's power cell as disclosed in the aforesaid patents.

Since the present apparatus includes two separate independent infusate reservoirs, different insulin concentrations can be contained in the apparatus. The main reservoir may contain insulin in a relatively low concentration to supply the basal requirements of the patient, while the secondary reservoir may contain insulin in a much higher concentration to provide the bolus doses for the patient. The ability of the apparatus to store and dispense insulin in both high and low concentrations means that the bolus needs of the patient can be supplied over a long term without depleting the supply of insulin.

In other words, whereas the prior apparatus of this type provide bolus doses simply by increasing the amount of flow of the same infusate used for the basal dose, the present apparatus delivers infusate at an entirely different concentration for the bolus dose. Also if the valve used to control bolus flow is electrically operated rather than mechanically actuated, its duty cycle is short so that a minimum amount of energy is required to power the valve. Still further, the total infusate volumetric requirements of the apparatus are minimized since it is no longer necessary to use relatively large volumes of low concentration infusate to provide the requisite bolus doses when called for by the patient's particular prescription.

While it is contemplated to use a battery powered electrical valve in the present apparatus, a preferred pump embodiment employs a valve that can be actuated extracorporeally either manually or magnetically. In this, the valve is mounted in the housing with its actuator situated directly under the patient's skin. Therefore by placing a magnet directly over that skin area or by depressing that skin area, the valve can be opened to initiate each bolus dose.

In some situations it is desirable to limit the bolus dose the apparatus can dispense within a selected time period to prevent possible injury to the patient. For example, a person may not remember that he has actuated the valve and received a bolus dose after a given meal and may actuate the valve two or more times within a short time interval. To avoid that potential problem, the present apparatus includes an auxiliary infusate reservoir or accumulator which may be similar to the others but which is quite small and connected in the fluid path from the bolus reservoir upstream from its valve.

Moreover, the outlet from the bolus reservoir includes a flow restricter which limits infusate flow from the bolus reservoir to the auxiliary reservoir so that the latter reservoir cannot be filled more than once in a given time period, e.g. 5 to 7 hours. Therefore, each time the patient actuates the valve to obtain a bolus dose of infusate, the maximum amount of infusate that he can obtain within that time period is the contents of the auxiliary reservoir, which contents will, for example, comprise one bolus dose or less. Thus, if the patient actuates the valve once after a given meal and due to forgetfulness actuates the valve again somewhat later, he will not receive any appreciable additional high concentrate infusate because the auxiliary reservoir will not have yet been refilled from the bolus reservoir.

In accordance with our techniques, the infusate concentrations, reservoir and mixing chamber volumes and flow rates to and from the chamber are selected to provide an integrated dosage profile from the apparatus, which is tailored to the patient's requirements. Thus the infusion technique of the present invention provides both the long term continuous basal infusate requirement of the patient and the intermittent larger bolus doses for a prolonged period between apparatus refills. Yet the apparatus used is relatively small and compact so that it causes a minimum amount of discomfort to the patient.

Further, the infusion apparatus can be operated to provide bolus flow by the patient himself with minimum risk of infusate overdose caused by excessive actuation of the bolus valve. More generally, the apparatus of this invention is rugged and reliable and can remain in the patient for a prolonged period without maintenance.

BRIEF DESCRIPTION OF THE DRAWINGS

For a fuller understanding of the nature and objects of the invention, reference should be had to the following detailed description taken in connection with the accompanying drawings, in which.

DESCRIPTION OF THE PREFERRED EMBODIMENTS

Figure 1:
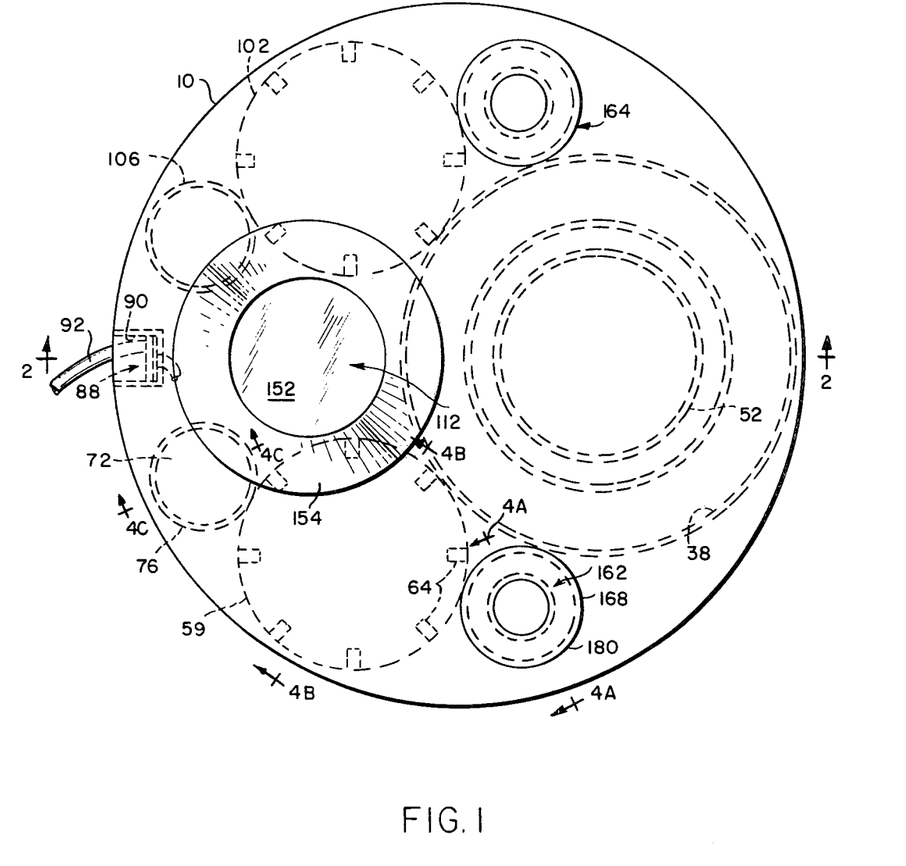
FIG. 1 is a top plan view of implantable infusion apparatus embodying the principles of this invention and for practicing our method.
Figure 2:
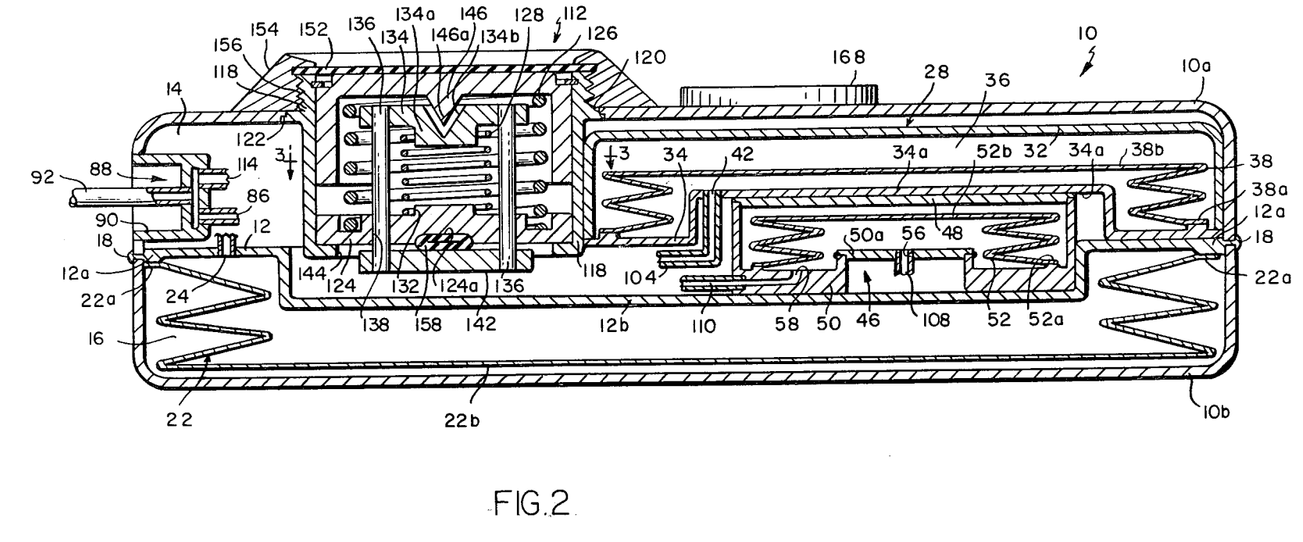
FIG. 2 is a sectional view along lines 2—2 of FIG. 1.

Referring first to FIGS. 1 and 2 of drawings, the infusion apparatus comprises a generally cylindrical housing 10 made of stainless steel, titanium or other strong corrosion resistant material. Typically housing 10 is on the order of three inches in diameter and one inch thick. Actually housing 10 is composed of a pair of upper and lower cup-like sections 10a and 10b which are secured together at their rims along with the edge 12c of a circular plate 12 which divides the housing into upper and lower compartments 14 and 16. That securement may be accomplished by a circumferential weld bead 18 or by other appropriate means. Plate 12 forms a header for a bellows capsule 22 situated in compartment 16. One end 22a of the bellows capsule is welded, brazed or otherwise secured to an edge margin of plate 12 just inside the weld bead 18. The opposite end 22b of the capsule is closed.

A circular central portion 12b of plate 12 inside the bellows capsule is dished downwardly as viewed in FIG. 2. Engagement of that portion by the bellows end wall 22b prevents excessive compression of the bellows which event might cause undue stresses on the capsule. The dished portion also maximizes the volume of housing compartment 14 and minimizes the residual or dead volume of the basal reservoir. Capsule 22 is preferably a titanium welded metal bellows and its diameter is slightly smaller than housing 10 to maximize the capsule volume, e.g., 20 ml. The space inside the capsule constitutes the main reservoir for infusate at the basal concentration, e.g., 20-30 units per milliliter. A fluid outlet from the confined volume of the capsule is provided at 24 in plate 12.

The space outside of capsule 22, yet inside compartment 16 is filled with a two-phase fluid of the type described in the aforesaid patents which vaporizes at physiological temperatures to provide sufficient force to collapse capsule 22 and expel infusate therefrom through its outlet 24. If the apparatus is dispensing infusate into the arterial system a pressure of about 6 psi will suffice. Venous or subcutaneous infusion requires less pressure, e.g. about 3 psi.

Still referring to FIGS. 1 and 2, situated in housing compartment 14 is secondary or bolus reservoir subassembly indicated generally at 28. Subassembly 28 comprises an inverted cup 32 nested in the top of housing section 10a near one side thereof. Cup 32 is provided with a circular cover 34 whose edge is welded or otherwise secured to the rim of cup 32 to form a closed compartment 36 inside the cup. One end 38a of a second or bolus bellows capsule 38 is secured to the inside of cover 34 near the outer edge thereof, the opposite capsule end 38b being closed. The central portion 34a of cover 34 inside the bellows capsule 38 is dished for the same reasons discussed above in connection with cover 12.

Capsule 38 is, like capsule 22, a welded metal bellows, its extended volume being about one-fifth that of capsule 22, e.g. 4 ml. The space inside bellows capsule 38 is the secondary infusate reservoir that contains the higher concentration infusate suitable for the bolus doses, e.g. 300-400 units per milliliter. A fluid outlet from the capsule is provided through an opening 42 in cover 34. The space outside capsule 38, but inside chamber 36 contains a two-phase fluid of the type described above in connection with capsule 22. At physiological temperatures that fluid exerts pressure on capsule 38, causing the capsule to collapse and expel its contents through opening 42.

Nested between cover portions 12b and 34a is a third or auxiliary reservoir subassembly indicated generally at 46. Subassembly 46 includes an inverted cup 50 having a generally circular cover 48 welded to its rim. A third bellows capsule 52 has one end 52a welded or otherwise secured to the inside of cover 50 near its edge and the opposite end 52b of the capsule is closed. The space inside capsule 52 constitutes an auxiliary reservoir or accumulator for bolus infusate.

to bias the capsule to its collapsed condition, the space outside capsule 52, yet inside cup 50 contains a compressible fluid, a spring or a two-phase fluid which, at body temperatures, exerts less pressure on capsule 52 than the similar fluid exerts on capsule 38 but enough to expel infusate into the patient's arterial or venous system. Capsule 52 is also a welded metal bellows and is quite small, being on the order of one-hundredth the volume of capsule 38, e.g. 0.04 ml. A fluid inlet to the capsule is provided through an opening 56 in a central recessed portion 50a of cover 50 and an outlet from capsule 52 is provided by a passage 58 in the cover near its edge.

Figure 4A:
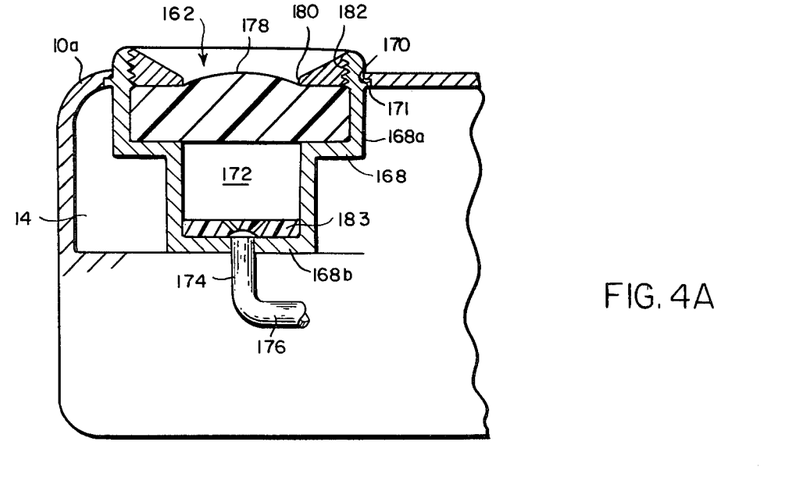
FIG. 4A is a similar view along lines 4A—4A of FIG. 1.
Figure 4B:
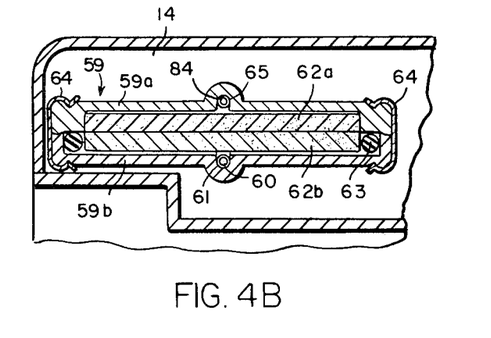
FIG. 4B is a similar view along lines 4B—4B of FIG. 1.

Referring now to FIGS. 1 and 4B, compartment 14 also includes a wafer-like filter unit 59 which receives infusate from bellows capsule 22 through a length of tubing 60 connected between capsule outlet 24 and filter inlet 61. All of the connecting tubing in the apparatus is quite small, e.g. 0.012 inch I.D.

Filter unit 59 comprises upper and lower circular shells 59a and 59b whose rims interfit so that the two sections form a cylindrical housing. Inside the housing are a pair of identical circular wafer-like filter support or retainer elements 62a and 62b made of porous stainless steel, titanium or other similar porous material. Sandwiched between the filter retainers is the filter element (not shown) providing filtration to about 0.22 microns. An O-ring 63 encircles element 62b inside shell 59b to provide a seal between the shell and the filter. The two shells are held together by C-lips 64 distributed around the edges of the filter unit 59. The filter inlet 61 is formed in the bottom wall of shell 59b and the filter outlet 65 is formed in the top wall of shell 59a.

Figure 4C:
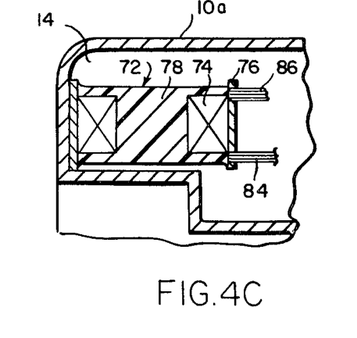
FIG. 4C is a similar view along lines 4C—4C of FIG. 1.

From filter unit 59, the infusate from capsule outlet 24 flows to a flow restricter 72 in housing compartment 14. As shown in FIG. 4C, the restricter 72 is simply a length of capillary tubing 74 coiled inside a ring 76, the space in and around the coil being filled with potting material 78. The restrictor can be of many configurations. See U.S. Pat. No. 3,951,147. The outlet 65 of filter 62 is connected by tubing 84 to one end of the coiled capillary tubing 74, the opposite end of the tubing being connected by tubing 86 to a mixing chamber indicated generally at 88 formed in a radially recessed portion 90 in the side wall of housing section 10a as best seen in FIG. 2. From the mixing chamber 88, the infusate is conducted by way of tubing 92 to an infusion site in the patient, the opposite end of tubing 92 being fitted with an appropriate catheter.

A second filter 102 is positioned in housing compartment 14 to receive the bolus infusate from bellows capsule 38. Fluid communication is achieved between those two components by a length of tubing 104 (FIG. 2) extending between the capsule outlet 42 and the filter inlet. Filter 102 is identical to filter 62 illustrated in FIG. 4B and accordingly it will not be detailed. From filter 102, the bolus infusate proceeds to a second flow restricter 106 which is, except for its length perhaps, identical to the restricter 72 illustrated in FIG. 4C. Therefore, we will not describe the restricter 106 in detail. The fluid output from restricter 106 is fed to the auxiliary bellows capsule 52 or accumulator by means of tubing 108 extending between the flow restricter and the capsule inlet 56. Infusate flow out of that capsule is through tubing 110 connected between capsule outlet 58 and a valve assembly mounted in housing compartment 14 and indicated generally at 112.

From the valve assembly, the bolus infusate is conducted by tubing 114 containing a flow restrictor 116 to mixing chamber 88. Restriction 116 is present simply for flow definition and smoothening purposes and that function may very well be provided by the regular tubing segment between the valve assembly and the chamber.

Figure 3:
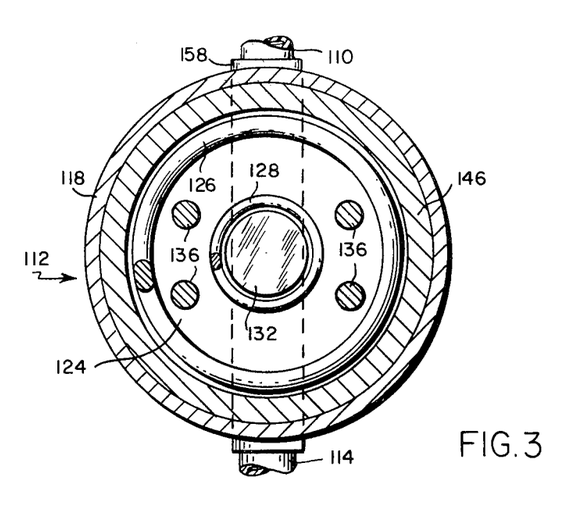
FIG. 3 is an enlarged sectional view along lines 3—3 of FIG. 2.

As best seen in FIGS. 2 and 3, valve assembly 112 comprises a generally cylindrical cup 118 which fits in an opening 120 formed in the top of housing section 10a so that a small length of the cup projects out through the top of the opening. A circumferential welded seam 122 connects the cup to housing section 10a. Positioned at the bottom of cup 118 is a circular disk 124 which supports a relatively heavy coil spring 126, the disk being grooved to center the spring. A second, lighter coil spring 128 positioned inside spring 126 also rests on disk 124 being centered there by a raised boss 132 on that disk.

Seated on the spring 128 inside spring 126 is a circular plate 134 having a central boss 134a projecting down into spring 128. Plate 134 supports the upper ends of four posts 136 which extend down between springs 126 and 128 and through loose-fitting openings 138 in disk 124. Connected to the lower ends of those posts is a circular plate 142, clearance for the plate being provided by an opening 144 in the bottom wall of cup 118.

The valve assembly also includes an actuating button 146 in the form of an inverted cup which fits down snugly inside cup 118 resting on the upper end of spring 126. Button 146 has a depending axial nose 146a which projects down into a mating opening 134b in the top of plate 134 to help center the components of the valve assembly. A flexible, resilient circular membrane 152 is positioned at the rim of cup 118 and retained there by a circular internally threaded ring 154 which is turned down onto external threads 156 on the projecting portion of cup 118. Membrane 152 provides a resilient impervious seal all around the button.

The final component of the valve assembly is a length of flexible resilient tubing 158 made of silastic or other comparable material sandwiched between disk 124 and plate 142. One end of the tubing communicates with tube 110 leading to the outlet of auxiliary bellows capsule 52. The other end of the tubing connects with the tube 114 leading to the restrictor 116 and mixing chamber 88. The flexible tubing is recessed into a groove 124a formed in the underside of disk 124 to maintain the tubing in a centered position in the assembly.

When there is no pressure on the button 146, both springs 126 and 128 are extended so that the button is in its uppermost position. In that position, the plate 134, being biased upwardly by spring 128, assumes its uppermost position thereby drawing plate 142 up along with it and squeezing the tubing 158 between plate 142 and disk 124 so that no fluid can flow through the tubing. On the other hand, when button 146 is depressed, the plates 134 and 142 are forced downwardly so that the tubing 158 assumes its normal cylindrical shape allowing fluid to flow from bellows capsule 52 to mixing chamber 88.

The advantage of utilizing the double spring arrangement illustrated in FIG. 2 is that the force which compresses the relatively delicate flexible tubing 158 is provided by the relatively light-weight spring 128. On the other hand, the heavy spring 126 determines the force required to depress button 146 sufficiently to open the valve. Desirably, the required actuating force should be relatively great so that the valve cannot be opened accidentally. In other words, a single spring could not provide both a relatively small squeezing force on tubing 158 and a relatively great return bias force on button 146.

Referring now to FIGS. 1 and 4A, provision is made in the present apparatus for refilling bellows capsules 22 and 38 with the basal and bolus infusate. More particularly, a self-sealing penetrable septum assembly shown generally at 162 is mounted at one side of housing section 10a through which infusate at the basal concentration can be injected into the apparatus to refill bellows capsule 22. A similar assembly indicated generally at 164 is located on the opposite side of housing section 10a.

Both of these septum assemblies are identical so that only the former one is illustrated in detail in FIG. 4A. It comprises a cup 168 positioned in an opening 170 in the top wall of housing section 10a, the rim of teh cup projecting above the housing wall. A circumferential weld 171 permanently connects the wall of the cup to the edge of opening 170 inside the housing section. Cup 168 has a relatively large diameter upper section 168a and a smaller diameter lower section 168b defining a cylindrical space 172. An opening 174 is provided in the bottom wall of cup 168 in which is connected one end of a tube 176 which leads to the bellows capsule 22.

Seated in the cup section 168a is a wafer-like penetrable septum or plug made of rubber or other comparable material. The septum is held in place by a ring 180 which is externally threaded so that it can be screwed or pressed down onto the projecting portion of cup 168 which carries internal threads 182. In the bottom of cup 168 is a needle stop 183 such as a wafer of teflon or other plastic material to receive the needle point during refill. Holes through the wafer allow the infusate to exit the chamber.

To refill capsule 22, a hypodermic needle is pierced through septum 178 so that is projects into chamber 172. Thence the infusate is injected into the chamber 172 whereupon it flows through tube 176 under the injection pressure to the bellows capsule 22. The incoming infusate extends the capsule and thereby compresses the two-phase fluid in housing compartment 16, thereby recharging the power cell that drives that capsule all as described in the aforesaid patents.

In the same fashion, capsule 52 is refilled and its power cell recharged by infusate injection through septum 164.

Figure 5:
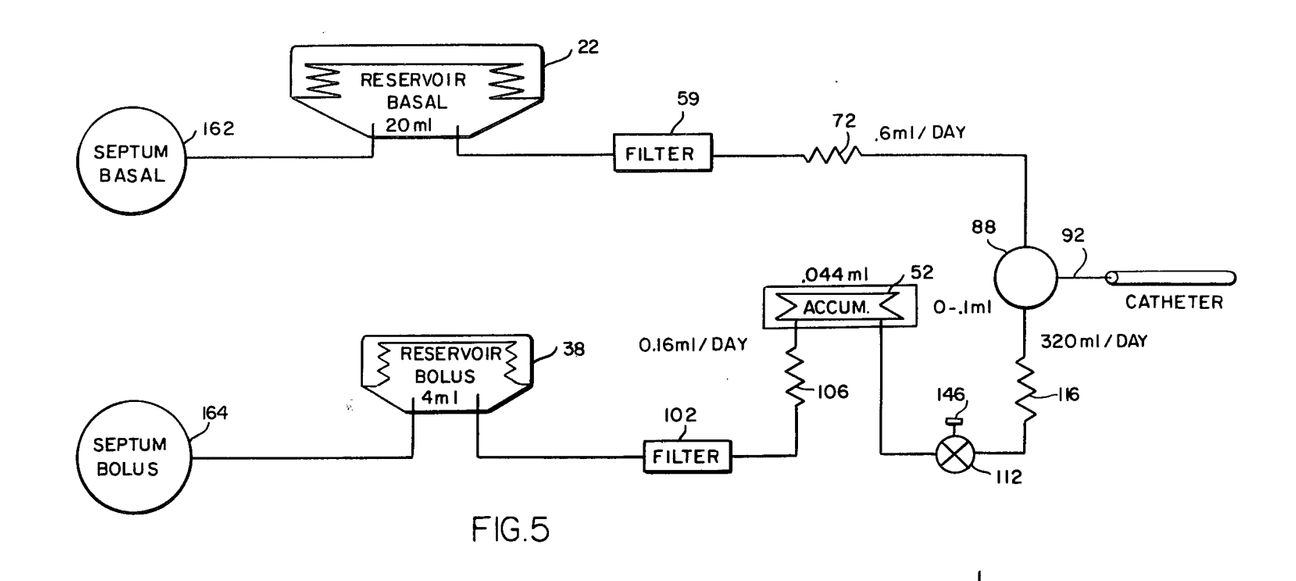
FIG. 5 is a diagrammatic view of the infusion apparatus of this invention.
Figure 6A:
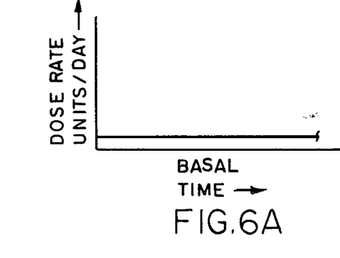
FIGS. 6A to 6B are graphical illustrations of valve functions and flow rates of the FIG. 5 system.
Figure 6B:
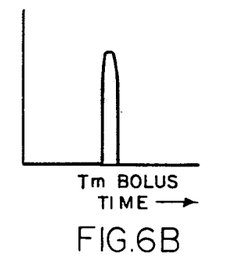
Figure 6C:
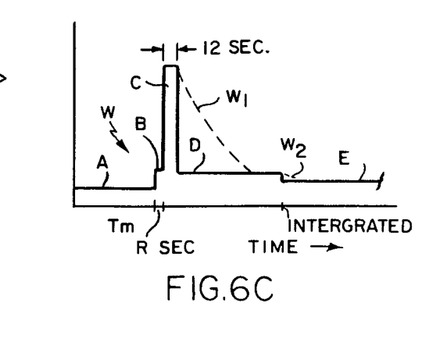

Refer now to FIG. 5 of the drawings which is a diagrammatic view showing more clearly the flow paths between the various infusion apparatus components and to the waveforms in FIGS. 6A to 6C depicting the basal, bolus and integrated unit flow rates for the apparatus in operation. For purposes of this description, we will assume that the basal reservoir 22 has been completely filled and charged by injection of infusate in the basal concentration through septum 162. Likewise, the bolus reservoir 38 has been filled and charged by injection of the bolus infusate through septum 164. Basal infusate flows through filter 59 and flow restricter 72 to the mixing chamber 88 at a very slow rate, e.g., on the order of 0.6 ml/day, the specific rate depending upon the particular patient's basal insulin requirement. From chamber 88 the infusate proceeds through tubing 92 to the catheter and into the patient's physiological system.

The infusate from the bolus reservoir 38, on the other hand, proceeds through filter 102 and flow restricter 106 at an even slower rate of about 0.16 ml/day to accumulator 52. The incoming infusate gradually extends the accumulator in opposition to the gas pressure or spring bias thereon until the accumulator is fully extended in which position it may hold, for example, 0.044 ml, constituting, say, one bolus infusion dose for a particular patient. Valve 112, being normally closed, prevents infusate flow from accumulator 52 to the mixing chamber 88. Accordingly as seen from FIG. 6A, the patient receives a continuous infusate dose at the basal concentration at a rate of about 0.6 ml/day.

Assume now that the patient consumes a meal at time $T_m$. At that time, the patient's blood sugar level normally tends to rise relatively dramatically so that the basal insulin dosage does not suffice to offset the increased glucose level in patient's bloodstream. The patient can actuate the valve 112 by manually depressing button 146 positioned under the patient's skin. The opening of that valve permits the accumulator 52 to expel its contents through the restrictor 116 to the mixing chamber 88 a relatively high rate for a very short time period, say 320 ml/day for several seconds or a few minutes. Even though accumulator 52 has a very small volume, it contains infusate in a high concentration presenting a large total bolus dose. Accordingly as seen from FIG. 6B, the dosage rate measured in infusate units per day is quite high, if short-lived, due to the high volumetric flow rate and the high drug concentration from the accumulator to the mixing chamber.

In chamber 88, the bolus infusate mixes with and supplements the basal infustate still arriving from the basal reservoir 22, with the integrated infusate dosage to the patient being reflected in FIG. 6C. As shown in that figure, the integrated flow rate is not simply the instantaneous sum of the basal and bolus rates illustrated in FIGS. 6A and 6B. Rather, it is a more complex function of reservoir volumes, infusate concentrations, flow path resistance, mixing chamber volume, outlet tube volume and valve-on-time.

More particularly, the segment of the FIG. 6C curve indicated at A denoting the basal infusate flow rate is, of course, a function of the basal infusate concentration and voumetric flow rate through restrictor 72 to the mixing chamber. When the patient activates valve 112 at meal time $T_m$, there is a rise in the total volumetric flow rate at the catheter due to infusate flow from the accumulator reservoir through the valve to the mixing chamber 88. At this time the increased concentration from the accumulator is not observed. This flow increase and does increase is reflected by the curve segment B in FIG. 6C. Assuming valve 112 is maintained in its open position sufficiently long to allow accumulator 52 to expel its entire contents, e.g. about 12 seconds, a bolus dose of high concentration infusate is issued to chamber 88 where it mixes with the basal infusate present there so that a short-lived "slug" of high concentration infusate at a high flow rate is dispensed to the patient as indicated by the curve segment C in FIG. 6C.

If the volume of the mixing chamber 88 approaches zero, the dose rate of infusate drops to a level that is still higher than the original basal rate, as indicated by the curve segment D in FIG. 6C (since the high volumetric flow rate has ceased, the dose is defined by the flow rate of restrictor 72 and the concentration in the bolus reservoir). The dose rate remains at that level for a relatively long period indicated which time duration depends upon the volumetric flow rate through restrictor 72 and the volume of liquid in the mixing chamber and the outlet catheter. After that time, the unit rate falls back to the original basal rate as the low concentration infusate at the flow rate for restrictor 72 mixes with and reduces the concentration of liquid in the mixing chamber as shown by curve segment E in FIG. 6C.

If, however, the volume of the mixing chamber 88 has an appreciable volume, say 0.1 ml, the infusion rate peak (because of mixing of basal and bolus concentrations) indicated in FIG. 6C trails off more or less in an expotential fashion as indicated by the dotted line curve $W_1$ in that figure. Likewise, the transition from the higher rate at curve segment D to the basal rate at segment E falls off expotentially as shown by the dotted line curved $W_2$ in FIG. 6C. The time constants of the curve segments $W_1$ and $W_2$ can be varied by varying the volume of chamber 88 the differences in drug concentrations and the flow rate through restrictor tube 72.

Thus, in the present apparatus, as soon as the valve 112 controlling the bolus flow is opened when the need arises, high concentration infusate is immediately dispensed to the patient with minimal system inertia. On the other hand, the desired dosage transition from the bolus back down to the basal rate may vary from patient to patient. For example, in one patient it may take a fairly long time for his glucose level to drop back to its ambient level after a meal due to physiological factors, while another patient may reach his nominal glucose level more quickly. The present apparatus is advantaged, then, in that its integrated infusate output to each patient can be tailored to suit his particular needs by proper selection of basal and bolus infusate concentrations mixing chmaber and catheter volume, restrictor flow rates and valve actuation time. Accordingly, the apparatus allows great flexibility in prescibing infusate to a patient over a prolonged period.

Also, because the apparatus dispenses high concentration infusate for the bolus doses, the low concentration basal supply is not depleted for that purpose as in prior apparatus of this type. The bolus reservoir can have a relativly small volume and the valve-open time of the valve 112 can be quite short thereby conserving energy in the event that an electrically operated valve is employed. Accordingly, the apparatus can remain implanted in the body for a prolonged period, e.g. a year or more, without having to be recharged, with only relatively infrequent, e.g. monthyl, infusate refills being required during that period.

Still referring to FIG. 5, it is important to note that the present apparatus also protects the patient from inadvertant bolus infusate overdoses in the event that valve 112 is opened repeatedly or is held in the open position. More particularly, each time valve 112 is opened by the patient, the maximum volume of bolus infusate that is dispensed to the patient is the contents of accumulator 52 representing, say, one bolus infusate dose. This is because the flow restrictor 106 between filter 102 and the accumulator is such that the accumulator is refilled from reservoir 38 at an extremely slow rate, e.g. 0.16 ml/day. Accordingly, even if the valve 112 remains open for a long time, e.g., an hour, the patient still receives not much more than one-quarter of the bolus dose of infusate.

By the same token, if the patient has actuated the valve at meal time and received a bolus dose to offset the increased blood sugar level caused by that meal and then inadvertently actuates the valve again a short time thereafter, he will receive only a very small amount of infusate because the accumulator 52 will not have been replenished with a significant amount of infusate from reservoir 38 during that time.

Thus while it is not required in the present apparatus, the provision of an accumulator located between an upstream very low flow rate restrictor from the bolus reservoir and a downstream valve constitutes a significant safety feature in apparatus such as this where the patient himself administers the bolus infusate doses. It should be understood, however, that even if the accumulator is not utilized, the present apparatus has the same advantages in terms of infusate dosage flexibility, reliability and power conservation described above.

Figure 7:
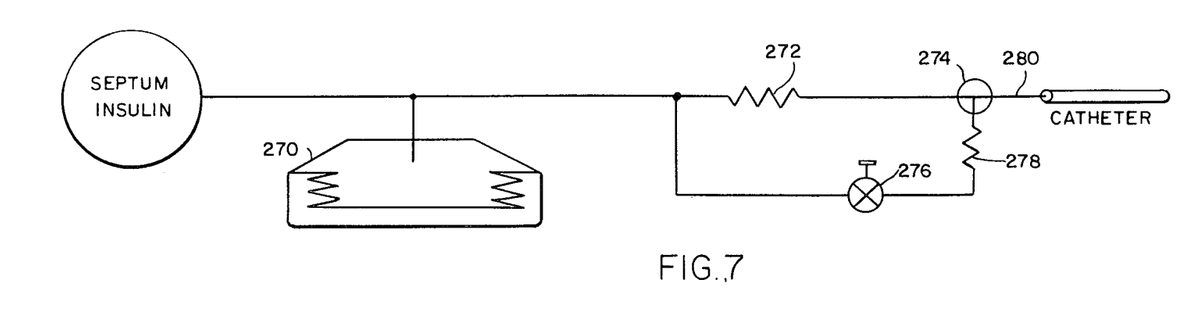
FIG. 7 is a schematic illustration of a modification of the FIG. 5 system.

When it is preferable that the implantable infusion apparatus employ two infusate reservoirs to conserve basal infusate and to minimize the valve 112 duty cycle, a modified embodiment has a single reservoir which, combined with valved and unvalved flow paths leading to an outlet will provide an integrated infusate dose similar to the one described above. FIG. 7 shows such an apparatus employing a single reservoir 270 connected by way of a flow restrictor 272 to a T fitting 274. A second flow path leading from reservoir 270 communicates with the fitting by way of a valve 276 and flow restrictor 278. The T fitting is, in turn, connected by way of a tube 280 to a catheter at the infusion site. Also, of course, an accumulator restrictor such as accumulator 52 with a restricted inlet can be provided upstream of valve 276 as in the case in the apparatus illustrated in FIG. 5.

Figure 8A:
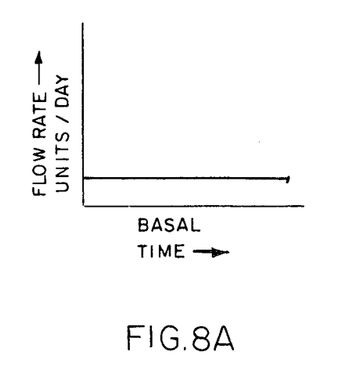
FIGS. 8A through 8C are graphical illustrations of flows in the FIG. 7 apparatus.
Figure 8B:
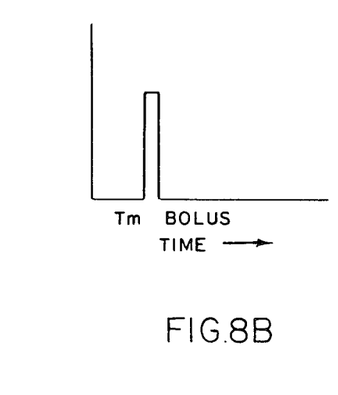
Figure 8C:
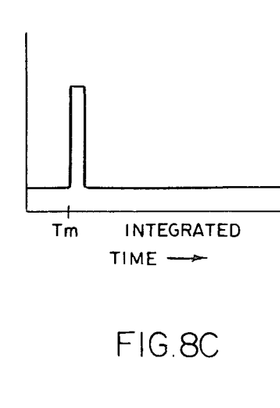

The restrictor 272 provides a relatively slow basal flow rate to chamber 274 as indicated by the waveform in FIG. 8A. On the other hand, the restrictor 278 provides for a much greater or substantially unrestricted bolus flow from reservoir 270 to the fitting 274 when the valve 276 is opened at meal time as indicated by the curve in FIG. 8B. The integrated unit dose rate that is dispensed at the infusion site is represented by the curve in FIG. 8C.

It will be seen from the foregoing, then, that the present implantable infusion apparatus dispenses infusate in one or more concentrations of one or more types at rates to suit the particular patient's requirements. Moreover, the infusate flow rate characteristics can be tailored with precision simply by modifying the flow rates and volumes of the apparatus components, particularly the mixing chamber and the apparatus outlet tube. Since the apparatus can dispense infusate in different concentrations, it can supply the patient's basal and bolus requirements in a minimum overall package so that the presence of the apparatus in the body is not unduly discomforting in terms of the space that it occupies in the body or in terms of the frequency with which it must be refilled or recharged.

It will also be seen that the objects set forth above, among those made apparent from the preceeding description, are efficiently attained, and since certain changes may be made in the above method and in the constructions set forth without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described.

We claim:

1. Non-electrical implantable infusion apparatus comprising
   A. a housing;
   B. a collapsible infusate reservoir having an outlet and positioned inside the housing;
   C. means for collapsing said reservoir to expel infusate from its said outlet;
   D. mixing means inside the housing and having a selected volume;
   E. a first flow path having a selected flow restriction characteristic connected between said reservoir and said mixing means;
   F. a second flow path having a selected flow restriction characteristic connected between said reservoir and said mixing means;
   G. a normally closed valve connected in the second flow path so that infusate flows from the reservoir to the mixing means along the second path only when said valve is opened, the infusates flowing along said first and second paths when said valve is opened supplementing one another in the mixing means to produce an integrated dosage, and
   H. a fluid outlet from the mixing means for conducting said integrated dosage out of the housing to an infusion site.

2. The infusion apparatus defined in claim 1 wherein the flow restriction characteristics of said first and second flow paths are different.

3. The infusion apparatus defined in claim 2 wherein the second flow path is less restrictive than the first flow path.

4. The infusion apparatus defined in claim 1 wherein said collapsing means comprises a two-phase fluid power cell associated with said reservoir, the fluid in said power cell vaporizing at physiological temperatures.

5. The infusion apparatus defined in claim 1 wherein said valve is mounted in said housing and is accessible from without said housing so that it can be operated manually transcutaneously when the apparatus is implanted subcutaneously.

6. The infusion apparatus defined in claim 5 wherein said valve comprises
  A. a length of flexible resilient tubing through which fluid flows between said reservoir and the mixing means along the second flow path when the valve is opened;
  B. means normally clamping said tubing preventing fluid flow therethrough, and
  C. means for selectively unclamping said clamping means.

7. The infusion apparatus defined in claim 6 wherein the clamping means comprises
  A. a stop member;
  B. a first clamp section engaging one side of the tubing;
  C. a button;
  D. first spring means reacting between the button and the stop member for biasing the first section against the stop member;
  E. a second clamp section engaging the opposite side of the tubing, and
  F. a second spring means biasing the second clamp section towards the first clamp section.

8. The infusion apparatus defined in claim 1 wherein the mixing means comprises a mixing chamber having a selected volume so that an integrated dosage containing a progressively lower contribution from the second flow path continues to flow to the infusion site for an appreciable time after said valve is closed.

9. The infusion apparatus defined in claim 1 and further including a valved passage leading from the outside of said housing to said reservoir by which said reservoir may be refilled with infusate.

10. The method of dispensing infusate inside a living body comprising the steps of:
  A. conducting infusate in a selected concentration or type at a selected flow rate along a first flow path to a mixing chamber;
  B. conducting said infusate at a selected flow rate along a second flow path to said mixing chamber;
  C. conducting the infusate from the mixing chamber along a third path to an infusion site in the body;
  D. normally blocking the infusate flow to the mixing chamber from the second flow path;
  E. momentarily unblocking the flow of infusate from the second flow path to the mixing chamber at determined time intervals so that in said chamber, infusate from the second flow path supplements infusate entering the mixing chamber from the first flow path, thereby providing an integrated dose to the infusion site, and
  F. relating the chamber volume and third flow rate so that when the flow from the second flow path to the mixing chamber is blocked, the contribution of the infusate from the second flow path to the integrated dose conducted to the infusion site falls off generally expotentially with a selected time constant.

11. The method defined in claim 10 and including the additional step of providing first and second flow paths having different fluid flow restriction characteristics to produce different flow rates through said paths.

12. The method defined in claim 11 including the added step of maing the second flow path less restrictive than the first flow path.

* * * * *

UNITED STATES PATENT AND TRADEMARK OFFICE
CERTIFICATE OF CORRECTION

PATENT NO. : 4,258,711
DATED : March 31, 1981
INVENTOR(S) : Elton M. Tucker, Frank R. Prosl It is certified that error appears in the above-identified patent and that said Letters Patent are hereby corrected as shown below:

Col. 1, line 8, change "956,558" to --856,558--.

Col. 1, line 46, change "4.077,405" to --4,077,405--.

Col. 2, line 45, change "or" to --of--.

Col. 5, line 15, change "6B" to --6C--.

Col. 5, line 24, change "of drawings" to --of the drawings--

Col. 6, line 33, change "to" to --To--.

Col. 6, line 62, change "C-lips" to --C-clips--.

Col. 7, line 22, change "stricter" to --strictor--.

Col. 7, line 23, change "restricter" to --restrictor--.

Col. 7, line 34, change "Restriction" to --Restrictor--.

Col. 8, line 50, change "teh" to --the--.

Col. 10, line 6, change "voumetric" to --volumetric--.

Col. 10, line 63, change "chmaber" to --chamber--.

Col. 11, line 9, change "monthyl" to --monthly--.

Col. 11, line 44, change "When" to --While--.

UNITED STATES PATENT AND TRADEMARK OFFICE
CERTIFICATE OF CORRECTION

PATENT NO. : 4,258,711

DATED : March 31, 1981

INVENTOR(S) : Elton M. Tucker, Frank R. Prosl

It is certified that error appears in the above-identified patent and that said Letters Patent are hereby corrected as shown below:

Col. 14, line 33, change "maing" to --making--.

Col. 14, insert missing claim as follows:

--13. Nonelectrical implantable infusion apparatus comprising
- A. a first collapsible infusate reservoir having an outlet opening;
- B. means for collapsing said reservoir to expel infusate from said outlet opening;
- C. a fluid outlet from the apparatus;
- D. a first flow path connected between said reservoir opening and said outlet;
- E. a second flow path connected between said reservoir opening and said outlet;
- F. a normally closed valve connected in the second flow path, and
- G. means for conducting the infusates from the first or second flow paths to an infusion site.--

On the Title Page, "12 Claims" should read -- 13 Claims --.

Signed and Sealed this

Fifteenth Day of September, 1981

[SEAL]

Attest:

GERALD J. MOSSINGHOFF

Attesting Officer    Commissioner of Patents and Trademarks